(12) United States Patent
Umeno et al.

(10) Patent No.: US 7,803,198 B2
(45) Date of Patent: Sep. 28, 2010

(54) HAIR DYE AND APPLICATOR FOR HAIR USING THE SAME

(75) Inventors: Takashi Umeno, Fujioka (JP); Keiichiro Takachiyo, Fujioka (JP); Hiroaki Koyama, Fujioka (JP)

(73) Assignee: Mitsubishi Pencil Company, Limited, Shinagawa-Ku, Tokyo (JP)

( * ) Notice: Subject to any disclaimer, the term of this patent is extended or adjusted under 35 U.S.C. 154(b) by 0 days.

(21) Appl. No.: 12/526,862

(22) PCT Filed: Feb. 12, 2008

(86) PCT No.: PCT/JP2008/052254

§ 371 (c)(1),
(2), (4) Date: Aug. 12, 2009

(87) PCT Pub. No.: WO2008/102666

PCT Pub. Date: Aug. 28, 2008

(65) Prior Publication Data

US 2010/0043151 A1 Feb. 25, 2010

(30) Foreign Application Priority Data

Feb. 23, 2007 (JP) ............................. 2007-043443

(51) Int. Cl.
*A61Q 5/10* (2006.01)
*C08F 226/06* (2006.01)

(52) U.S. Cl. ..................... 8/405; 8/435; 8/455; 8/463; 8/552; 8/554; 8/555; 8/558; 8/568; 8/570; 8/606; 526/258

(58) Field of Classification Search ............ 8/405, 8/435, 455, 463, 552, 554, 555, 558, 568, 8/570, 606; 526/258
See application file for complete search history.

(56) References Cited

U.S. PATENT DOCUMENTS

| 6,207,778 B1 * | 3/2001 | Jachowicz et al. .......... 526/258 |
| 6,905,521 B2 | 6/2005 | Tsuchiya |
| 2004/0205901 A1 | 10/2004 | Cottard et al. |

FOREIGN PATENT DOCUMENTS

JP 2001-172141 A 6/2001

(Continued)

OTHER PUBLICATIONS

STIC Search Report dated May 4, 2010.*

(Continued)

*Primary Examiner*—Eisa B Elhilo
(74) *Attorney, Agent, or Firm*—Buchanan Ingersoll & Rooney PC

(57) ABSTRACT

Provided is a hair dye comprising 0.1 to 3.0% by weight of at least one of aqueous acid dyes and a resin comprising a terpolymer constituted from a vinyl cyclic amide, an acrylic acid derivative and a quaternary derivative of acrylic acid, wherein a content of the resin is 0.1 to 2.5% by weight in terms of a solid content; and the hair dye further comprises 1.0 to 20% by weight of a hair dyeing auxiliary agent, 20 to 60% by weight of a lower alcohol and 20 to 60% by weight of water and has a pH of 2 to 4.

9 Claims, 8 Drawing Sheets

FOREIGN PATENT DOCUMENTS

| JP | 2002-104942 A | 4/2002 |
|---|---|---|
| JP | 2002-544299 A | 12/2002 |
| JP | 2003-40746 A | 2/2003 |
| JP | 2004-520369 A | 7/2004 |
| JP | 2004-250394 A | 9/2004 |

OTHER PUBLICATIONS

International Search Report (PCT/ISA/210) for PCT/JP2008/052254 completed Mar. 6, 2008.

Notification of Transmittal of Copies of Translation of the International Preliminary Report on Patentability (Form PCT/IB/338), International Preliminary Report on Patentability (Form PCT/IB/373), Written Opinion of the International Search Authority (Form PCT/ISA/237) mailed in corresponding International Patent Application No. PCT/JP2008/052254, Sep. 11, 2009, The International Bureau of WIPO, Geneva, CH.

* cited by examiner

HAIR DYE AND APPLICATOR FOR HAIR USING THE SAME

TECHNICAL FIELD

The present invention relates to a cumulatively dyeing hair dye which does not require washing of hair immediately after used and by which the hair are gradually dyed every time using it reaptedly. More specifically, it relates to a hair dye which is excellent in water resistance and which is excellent as well in a cumulative hair dyeing property and usability and an applicator for hair using the above hair dye.

BACKGROUND ART

Permanent hair dyes (oxidizing hair dyes) and semi-permanent hair dyes (acid hair dyes) which have so far usually been used have such large defects that dyeing operation in use is complicated and troublesome and that the circumference, cloths and the skin of users are dyed.

Accordingly, they have to be applied usually in beauty solons or they have to be applied by ourselves in bathing so that they can be washed away soon even if stained, and therefore an excessive burden has been forced to the users.

A cumulatively dyeing temporary hair dye (refer to patent document 1) provided by the present applicant which comprises 0.01 to 3% by weight of an acid dye as a coloring agent, 1.5 to 10% by weight of a nonionic or anionic silicone base resin, 3 to 20% by weight of a hair dyeing auxiliary, 30 to 80% by weight of a lower alcohol and 5 to 50% by weight of water and which has a pH of 2 to 5 and a viscosity of 100 mPa·s or less is known as a hair dye which can reduce the above burden and which can cumulatively dye hair by using repeatedly with simplicity even if a dyeing amount per once is small.

Further, known are an acid hair dye composition (patent document 2) prepared by blending 0.01 to 1% of at least one of acid dyes, 0.1 to 10% of an acid as a pH controlling agent, 1 to 20% of an aromatic alcohol as a penetrant, 1 to 20% of a lower alcohol as a solvent and 0.01 to 5% of a polymer compound as a thickener and an acid hair dye composition (patent document 3) prepared by blending 0.01 to 10.0% of at least one of amino-modified or ammonium-modified polymer silicones represented by a specific formula.

The hair dye described in patent document 1 is excellent as a hair dye which can cumulatively dye hair, but it is a little inferior in water resistance. Also, the acid hair dye compositions described in patent documents 2 and 3 described above are common in terms of using acid dyes, but they involve problems in terms of being inferior in water resistance and a hair dyeing property. Further, they have a high viscosity and therefore have such a problem in terms of usability that they are not unsuited to use with an applicator for hair having an occlusion body such as a sliver and the like.

Patent document 1: Japanese Patent Application Laid-Open No. 2001-172141
Patent document 2: Japanese Patent Application Laid-Open No. 2002-104942
Patent document 3: Japanese Patent Application Laid-Open No. 2003-40746

DISCLOSURE OF THE INVENTION

Problems to be Solved by the Invention

In light of the problems of the conventional art described above, the present invention intends to solve them, and an object thereof is to provide a hair dye which is excellent in water resistance and usability and which is excellent as well in a cumulative hair dyeing property and an applicator for hair using the above hair dye.

Means for Solving the Problems

Intensive studies repeated by the present inventors on the problems of the conventional art described above have resulted in finding that a hair dye meeting the object described above and an applicator for hair using the hair dye are obtained by using an aqueous acid dye, a resin comprising a specific terpolymer, a hair dyeing auxiliary agent, a lower alcohol and water and controlling the contents thereof respectively in specific ranges, and thus the present invention has come to be completed.

That is, the present invention comprises the following items (1) to (9).

(1) A hair dye comprising 0.1 to 3.0% by weight of at least one of aqueous acid dyes and a resin comprising a terpolymer constituted from a vinyl cyclic amide represented by following Formula (I), an acrylic acid derivative represented by following Formula (II) and a quaternary derivative of acrylic acid represented by following Formula (III), wherein a content of the resin is 0.1 to 2.5% by weight in terms of a solid content; and the hair dye further comprises 1.0 to 20% by weight of a hair dyeing auxiliary agent, 20 to 60% by weight of a lower alcohol and 20 to 60% by weight of water and has a pH of 2 to 4:

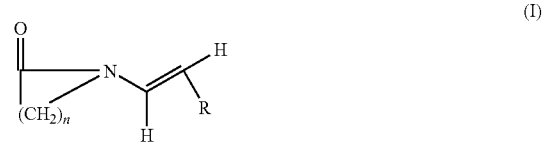

(in Formula (I), n is an integer of 3 to 6, and R represents a hydrogen atom or an alkyl group having 1 to 5 carbon atoms);

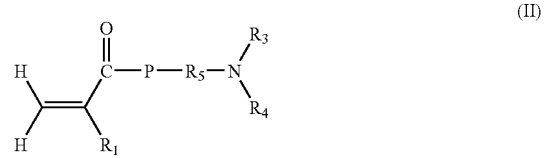

(in Formula (II), P is an oxygen atom or $NR_2$; $R_1$, $R_2$, $R_3$ and $R_4$ each are a hydrogen atom or an alkyl group having 1 to 5 carbon atoms, and they may be the same or different; and $R_5$ represents an alkylalkylene group having 2 to 16 carbon atoms);

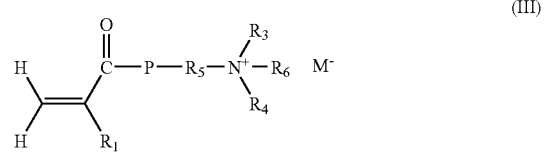

(in Formula (III), P is an oxygen atom or $NR_2$; $R_1$, $R_2$, $R_3$ and $R_4$ each are a hydrogen atom or an alkyl group having 1 to 5 carbon atoms, and they may be the same or different; $R_5$ represents an alkylalkylene group having 2 to 16 carbon atoms; $R_6$ is an alkyl group having 9 to 24 carbon atoms; and M represents a halide, tosylate or phosphoric acid anion).

(2) The hair dye as described in the above item (1), wherein the resin is constituted from 60 to 90% by weight of a vinyl cyclic amide represented by Formula (I), 5 to 30% by weight of an acrylic acid derivative represented by Formula (II) and 1 to 30% by weight of a quaternary derivative of acrylic acid represented by Formula (III).

(3) The hair dye as described in the above item (1) or (2), wherein the resin has a weight average molecular weight of 400000 to 800000.

(4) The hair dye as described in any one of the above items (1) to (3), wherein a content ratio y (% by weight) of the aqueous acid dye satisfies following Formula (IV) assuming that a solid content of the resin is x (% by weight):

$$0.1(x+1) < y \leq 0.264x + 0.4 \quad \text{(IV)}$$

(5) The hair dye as described in any one of the above items (1) to (4), wherein a content ratio (A)/[(A)+(B)] of water (A) to the lower alcohol (B) is 0.3 to 0.8 in terms of a weight ratio.

(6) The hair dye as described in any one of the above items (1) to (5), wherein the hair dyeing auxiliary agent is at least one selected from monohydric alcohols, polyhydric alcohols, ether alcohols, lower alkylene carbonates, N-alkylpyrrolidones and lactones.

(7) The hair dye as described in any one of the above items (1) to (6), wherein a viscosity of the hair dye is 2 to 50 mPa·s.

(8) An applicator for hair having a storing part for storing the hair dye as described in any one of the above items (1) to (7).

(9) The applicator for hair as described in the above item (8), wherein an applying main body part comprising an applying body for applying a hair dye on hair and a comb part disposed on a periphery of the applying body is mounted at a tip part of an applicator main body.

Effects of the Invention

According to the present invention, a hair dye which is free from skin irritation and excellent in water resistance and an applying performance and which is excellent as well in a cumulative hair dyeing property and a drying property.

The applicator for hair according to the present invention does not cause "blobbing" and involuntary discharge of liquid and is excellent in carrying and handling, and it is excellent as well in water resistance and a cumulative hair dyeing property.

BEST MODE FOR CARRYING OUT THE INVENTION

The embodiments of the present invention shall be explained below in details.

The hair dye of the present invention comprises 0.1 to 3.0% by weight of at least one of aqueous acid dyes and a resin comprising a terpolymer constituted from a vinyl cyclic amide represented by following Formula (I), an acrylic acid derivative represented by following Formula (II) and a quaternary derivative of acrylic acid represented by following Formula (III), wherein a content of the resin is 0.1 to 2.5% by weight in terms of a solid content; and the hair dye further comprises 1.0 to 20% by weight of a hair dyeing auxiliary agent, 20 to 60% by weight of a lower alcohol and 20 to 60% by weight of water and has a pH of 2 to 4:

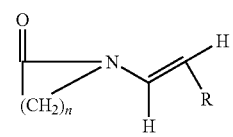

(in Formula (I), n is an integer of 3 to 6, and R represents a hydrogen atom or an alkyl group having 1 to 5 carbon atoms);

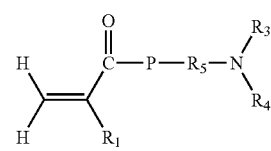

(in Formula (II), P is an oxygen atom or $NR_2$; $R_1$, $R_2$, $R_3$ and $R_4$ each are a hydrogen atom or an alkyl group having 1 to 5 carbon atoms, and they may be the same or different; and $R_5$ represents an alkylalkylene group having 2 to 16 carbon atoms);

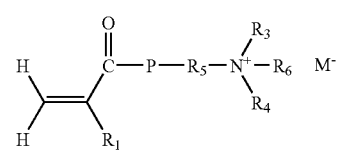

(in Formula (III), P is an oxygen atom or $NR_2$; $R_1$, $R_2$, $R_3$ and $R_4$ each are a hydrogen atom or an alkyl group having 1 to 5 carbon atoms, and they may be the same or different; $R_5$ represents an alkylalkylene group having 2 to 16 carbon atoms; $R_6$ is an alkyl group having 9 to 24 carbon atoms; and M represents a halide, tosylate or phosphoric acid anion).

The aqueous acid dye used in the present invention shall not specifically be restricted as long as it is allowed to be used for hair dyes and classified into water-soluble acid dyes, and capable of being used is one compound or a mixture of two or more compounds selected from compounds which exhibit no harmful action to human bodies and are permitted to be used for coloring medicines, quasi drugs and cosmetics and which are prescribed by "Ministerial ordinance prescribing tar colors capable of being used for medicines and the like" (Notification of Ministry of Health and Welfare in 1966).

The specific examples of the aqueous acid dye involves at least one (alone or a mixture of two or more kinds thereof; hereinafter the same shall apply) of Red No. 3 (Erythrosine), Red No. 102 (New Coccine), Red No. 207 (Lithol Red BA), Orange No. 205 (Orange II), Yellow No. 4 (Tartrazine), Yellow No. 402 (Polar Yellow 5G), Yellow No. 403 (1) (Naphthol Yellow S), Green No. 3 (Fast Green FCF), Green No. 204 (Pyranine Conc.), Blue No. 1 (Brilliant Blue FCF), Blue No. 202 (Patent Blue NA), Purple No. 401 (Arizurol Purple), Brown No. 201 (Resorcin Brown), Black No. 401 (Naphthol Blue Black), but they shall not be restricted to the above compounds.

A content of the above aqueous acid dyes has to be 0.1 to 3.0% by weight (hereinafter referred to merely as "%") based on the total amount of the hair dye, and it is preferably 0.1 to 1%.

If a content of the aqueous acid dye is less than 0.1%, the hair dyeing effect is not sufficiently exerted, and if it exceeds 3%, stain toward the other parts such as the skin is liable to be caused. Accordingly, both are not preferred.

The resin (hereinafter referred to merely as "the terpolymer") comprising a terpolymer used in the present invention is a resin which is suited for allowing the water resistance to be consistent with the cumulative hair dyeing property to a high degree and reducing a viscosity of the hair dye, and it is the resin comprising the terpolymer constituted from a vinyl cyclic amide represented by Formula (I), an acrylic acid derivative represented by Formula (II) and a quaternary derivative of acrylic acid represented by Formula (III).

The resin comprising the terpolymer constituted from 40 to 95% of the vinyl cyclic amide represented by Formula (I), 0.1 to 55% of the acrylic acid derivative represented by Formula (II) and 0.25 to 50% of the quaternary derivative of acrylic acid represented by Formula (III) is preferably used from the viewpoints of water solubility and water resistance after drying, and the resin comprising the ternary polymer constituted from 60 to 90% of the vinyl cyclic amide represented by Formula (I), 5 to 30% of the acrylic acid derivative represented by Formula (II) and 1 to 30% of the quaternary derivative of acrylic acid represented by Formula (III) is more preferably used.

The terpolymer used in the present invention is a cationic polymer which is modified so that it is hydrophobic, and it has long chain alkyl therein. The typical terpolymer is constituted from vinyl pyrrolidone represented by Formula (I), dimethylaminopropylacrylamide (DMAPAA) represented by Formula (II) and an alkyl quaternary derivative of DMAPAA represented by Formula (III) in which the alkyl has 12 to 18 carbon atoms, more preferably 12 carbon atoms, wherein a content of the compound represented by Formula (I) is 60 to 90%; that of the compound represented by Formula (II) is 5 to 30%; and that of the compound represented by Formula (III) is 1 to 30%. It is, for example, a polymer represented by the following formula:

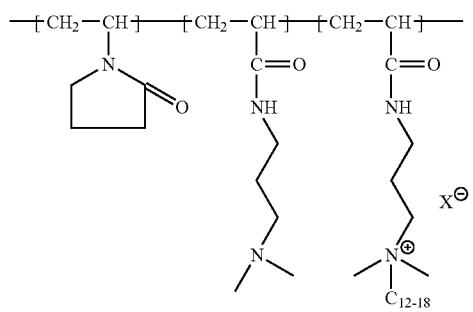

Alkyldimethylaminopropylacrylamide which is the compound represented by Formula (III) described above is preferably prepared by tosylating DMAPAA as shown below:

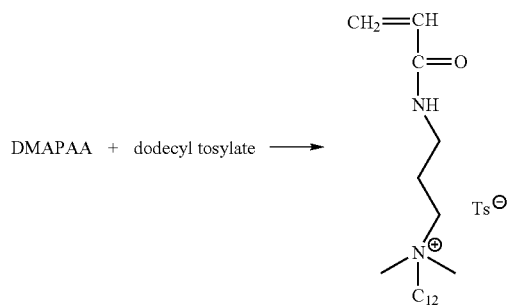

The terpolymer used in the present invention is preferably a terpolymer which has a weight average molecular weight of 200,000 to 2,000,000, preferably 400,000 to 800,000 and is water-soluble or water-dispersible and which forms, when cast on a surface of a support, an apparently moisture resistant and hydrophobic film, wherein the film is surface-active and stable against hydrolysis, and the terpolymer is more preferably homogeneous.

The usable commercial products of the terpolymer involve STYLEZE W-10 (obtained by controlling Polyquaternium 55 (manufactured by ISP Ltd.) to a resin solid content of 10%), STYLEZE W-20 (obtained by controlling Polyquaternium 55 (manufactured by ISP Ltd.) to a resin solid content of 20%) and the like.

The above terpolymers have to be controlled to 0.1 to 2.5% in terms of a solid content, preferably 0.1 to 1.5% and more preferably 0.3 to 1.0% based on the total amount of the hair dye.

If a content of the terpolymer is less than 0.1%, the sufficiently high water resistance is not attained. On the other hand, if it exceeds 2.5%, the cumulative hair dyeing property is reduced, and a viscosity of the liquid is too high, so that it is less liable to be handled.

The hair dyeing auxiliary agent used in the present invention is added in order to exhibit more hair dyeing effect and includes, for example, at least one selected from monohydric alcohols, polyhydric alcohols, ether alcohol, lower alkylene carbonates, N-alkylpyrrolidones and lactones.

To be specific, monohydric alcohols which are not involved in the lower alcohols described above as the hair dye component can be used as the monohydric alcohol, and it involves benzyl alcohol, phenethyl alcohol, furfuryl alcohol, cyclohexanol and the like. The polyhydric alcohol involves ethylene glycol, propylene glycol, 1,3-butylene glycol, glycerin, diglycerin, dipropylene glycol and the like. The ether alcohol involves methyl cellosolve, ethyl cellosolve, butyl cellosolve, methyl carbitol, ethyl carbitol, propyl carbitol, butyl carbitol and the like. The lower alkylene carbonate involves ethylene carbonate, propylene carbonate, butylene carbonate and the like. The N-alkylpyrrolidones (lactams) involve N-methylpyrrolidone (N-methyl-2-pyrrolidone), N-ethylpyrrolidone, N-octylpyrrolidone and the like. The lactones involve γ-butyrolactone and the like. They can be used alone or in a mixture of two or more kinds thereof.

Benzyl alcohol, N-methylpyrrolidone (N-methyl-2-pyrrolidone), propylene carbonate and the like are preferred in terms of safety, a drying property and an odor.

A content of the above hair dyeing auxiliary agents is preferably 1 to 20%, more preferably 5 to 15% based on the total amount of the hair dye.

If a content of the hair dyeing auxiliary agent is less than 1%, the hair dyeing effect is not sufficiently exerted. On the other hand, if it exceeds 20%, the drying property after applying is reduced. Accordingly, both are not preferred.

At least one of lower alcohols which can be used for hair dyes, such as ethanol, propanol, butanol, isopropanol, isobutanol and the like can be used as the lower alcohol for the present invention, and ethanol is preferably used in terms of safety, a drying property and an odor.

A content of the lower alcohol described above has to be 20 to 60% based on the total amount of the hair dye, and it is preferably 20 to 45%.

If a content of the lower alcohol is less than 20%, the drying property is reduced, and if it exceeds 60%, the hair dyeing effect is not sufficiently exerted. Accordingly, both are not preferred.

The balance of the hair dye in the present invention is controlled by water, and refined water, distilled water, ion-exchanged water, purified water, ultrapure water, clean water, aqua and the like can be used. A content thereof has to be 20 to 60% based on the total amount of the hair dye, and it is preferably 35 to 60%.

If a content of water is less than 20%, the hair dyeing effect is reduced, and if it exceeds 60%, the drying property and the low temperature stability are reduced. Accordingly, both are not preferred.

Other optional components can suitably be added to the hair dye of the present invention as long as the effects of the present invention and stability of the system are not damaged, and capable of being added are, for example, various surfactants, antiseptic agents, antioxidants, reduction inhibitors, chelating agents, UV absorbers, viscosity controlling agents, oil components, silicone derivatives, pigments, fragrances, animal and plant extracts, well-known polymer components and the like.

In the hair dye of the present invention, the aqueous acid dye and the resin comprising the terpolymer described above are factors exerting an effect on the hair dyeing property and the water resistance, and they are added in the ranges of the respective contents described above. From the viewpoint of improving further more the hair dyeing property and the water resistance, the following Formula (IV) is more preferably satisfied assuming that a content ratio of the aqueous acid dye is y (% by weight) and that a solid content of the resin comprising the terpolymer described above is x (% by weight):

$$0.1(x+1) < y \leq 0.264x + 0.4 \quad (IV)$$

For example, when a content of the aqueous acid dye is 0.5% by weight, a solid content x of the resin used is preferably 0.379 ($\approx$0.3787878...) % by weight or more (to 2.5% by weight).

Further, in the hair dye of the present invention, water and the lower alcohol are factors exerting an effect on stability and a hair dyeing property of the resin comprising the terpolymer dissolved in the hair dye, and they are added in the ranges of the respective contents described above. From the viewpoint of improving further more the stability and the hair dyeing property, a content ratio (A)/[(A)+(B)] of water (A) to the lower alcohol (B) is preferably 0.3 to 0.8 in terms of a weight ratio.

In the hair dye of the present invention, pH is set to 2 to 4 from the viewpoints of using the aqueous acid dye and preventing hair damage and skin irritation.

If a pH of the hair dye exceeds 4, the hair dyeing property is unsatisfactory, and therefore it is not preferred. On the other hand, if the pH is less than 2, irritation to the skin and damage to the hair are brought about in a certain case, and therefore it is not preferred.

In the present invention, the pH can be controlled by optionally using conventional pH controlling agents, for example, organic and inorganic bases such as triethanolamine, potassium hydroxide, sodium hydroxide and the like and organic and inorganic acids such as citric acid, malic acid, hydrochloric acid, glycolic acid and the like.

A viscosity of the hair dye of the present invention is 2 to 50 mPa·s, preferably 3 to 30 mPa·s from the viewpoint of readily applying it onto hair.

If a viscosity of the hair dye is less than 2 mPa·s, it is liable to be adhered onto the scalp, and it is liable to be spattered to stain the cloth. On the other hand, if it exceeds 50 mPa·s, it is difficult to spread the hair dye thinly and evenly on the hair. Accordingly both are not preferred.

The hair dye in the present invention can be produced by blending the respective components such as the aqueous acid dye, the terpolymer, the hair dyeing auxiliary agent, the lower alcohol, water and the like each described above in the ranges of the respective contents described above and evenly stirring and mixing them.

The hair dye of the present invention thus constituted can suitably be used as a hair color for black hair, a hair color for gray hair and the like, and obtained is the hair dye which does not dye the skin and is excellent in a cumulative dyeing property and which has excellent water resistance against sweat, rain and the like in a hot humid season such as a summertime and is excellent in usability. In particular, it functions as a primary coloring agent which does not cause skin irritation even when applied on the hair in a wide range and is excellent in a drying property and which can be used over an extended period of time after dried and can sufficiently endure rain and sweat. Further, it is endowed with such an excellent cumulative hair dyeing property and usability that the color remains on the hair even after washing the hair and that the hair are gradually dyed by repeatedly using the hair dye.

An applicator for hair is used in using the hair dye of the present invention thus constituted, and the applicator for hair used shall not specifically be restricted in a form, a structure and the like.

In the present invention, the applicator for hair which can be used involves preferably, from the viewpoints of applying on the hair, controlling a liquid amount supplied to the applying part, less stain caused on cloths, skins, furniture and the like and usability, an applicator for hair having a storing part for storing the hair dye of the present invention, and involves more preferably an applicator for hair in which an applying main body part comprising an applying body for applying a hair dye on hair and a comb part disposed on a periphery of the applying body is mounted at a tip part of the applicator main body.

FIG. 1 shows an applicator A for hair showing one example of the embodiment of an applicator for hair in which the hair dye of the present invention is used.

The above applicator A for hair is an applicator equipped with a valve device of a knocking type. As shown in FIG. 1, a pedestal 11 is fixed at a tip part of an applicator main body 10, and an applying body 12 comprising brush bodies 12a, 12a ... of 7 brushes×2 lines is provided at the above pedestal 11. Further, a tip shaft 13 is fixed on a circumference of the pedestal 11, and a comb body 15 equipped with comb parts 15a, 15a ... of 9 combs×2 lines is detachably mounted at the above tip shaft 13. An impregnation body 16 comprising a sponge and the like which is brought into contact with the applying body 12 is inserted into a central hole of the pedestal 11, and a hair dye introducing tube 18 communicated with a tip of a valve device described later is provided at the back of the pedestal 11 interposing an impregnation body stopper 17 therebetween. Meanwhile, 19 is a cap body.

Also, a cylindrical inner barrel 20 which is a hair dye storing part is provided in the applicator main body 10, and a valve device 25 comprising a valve rod 21, a valve seat 22, a valve spring 23 and a spring receiver 24 is mounted at a tip part thereof. A knocking body 26 is provided at a rear end part thereof. Meanwhile, 27 is a stirring ball.

In the applicator A for hair thus constituted, the storing part 20 is filled with the hair dye constituted as described above, and the hair dye flows into the impregnation body 16 via the hair dye introducing tube 18 by clicking the knocking body 26 and is supplied to the applying body 12 comprising the brush bodies 12a, 12a ..., whereby it is used.

The above applicator A for hair assumes a structure in which the hair dye is supplied from the impregnation body 16 to the applying body 12 comprising the brush bodies 12a, 12a ..., and therefore it does not cause "blobbing" and involuntary discharge of the liquid. Further, since it has the comb body 15, the hair dye is not adhered directly on fingers and so on, and it can be the applicator for hair which is excellent in carrying and handling and which is excellent as well in usability, water resistance and a cumulative hair dyeing property.

FIG. 2 and FIG. 3 show an applicator B for hair showing another example of the embodiment of an applicator for hair in which the hair dye of the present invention is used.

In the above applicator B for hair, as shown in FIG. 2 and FIG. 3, an occluding body 31 occluding the hair dye of the present invention is mounted in a hair dye storing part 30a in the inside of a barrel body 30 constituting an applicator main body; plural comb-like feeds 32 having capillary action for applying are fixed at a tip part of the barrel body 30 in an arrangement of a linear line, and rear end parts of the feeds 32 are connected with the occluding body 31; a tip part of the feed 32 is protruded to the front of the barrel body 30; comb parts 33 are provided at a side part of the feed 32; a cap main body 40 is detachably disposed at a tip part of the barrel body 30 by screwing; a feed tip receiving member 41 of a felt or the like with which a tip part of the feed 32 is brought into contact is mounted; an inner cap 43 in which a concave part 42 receiving a tip part of the comb part 33 is provided at a side part thereof is arranged in the inside of the cap main body 40 movably in an axial direction and rotatably in a circumferential direction to assume a state in which the inner cap 43 is pushed in an opening direction of the cap main body 40 by means of a spring member 44.

In the applicator B for hair thus constituted, the required hair dye is supplied from the occluding body 31 occluding the hair dye of the present invention in the hair dye storing part 30a to a tip part of the feed 32 which is an applying part, and it does not cause "blobbing" and involuntary discharge of liquid. It can be the applicator for hair which is excellent in carrying and handling and which is excellent as well in usability, water resistance and a cumulative hair dyeing property.

FIG. 4 to FIG. 6 show an applicator C for hair showing another example of the embodiment of an applicator for hair in which the hair dye of the present invention is used.

The above applicator C for hair is a modified example of the applicator B for hair shown in FIG. 2 and FIG. 3, and as shown in FIG. 4 to FIG. 6, an occluding body 51 occluding the hair dye of the present invention is mounted in a hair dye storing part 50a in the inside of a barrel body 50 constituting an applicator main body; plural comb-like feeds 52 having capillary action for applying are detachably fixed at a tip part of the barrel body 50 in an arrangement of a linear line, and rear end parts of the feeds 52 are connected with the occluding body 51; a tip part of the feed 52 is protruded to the front of the barrel body 50; comb parts 53 are detachably provided at a side part of the feed 52; a cap main body 54 is detachably disposed at a tip part of the barrel body 50 by screwing; an inner cap 55 receiving a tip part of the comb part 53 provided at a side part of the feed 52 is arranged in the inside of the cap main body 54 movably in an axial direction and rotatably in a circumferential direction to assume a state in which the inner cap 55 is pushed in an opening direction of the cap main body 54 by means of a spring member 56. Meanwhile, 57 is an external cylinder disposed between the cap main body 54 and the inner cap 55, and 58 and 59 are a middle cap member and a rear cap member which cover a rear end part of the barrel body 50.

In the above applicator C for hair thus constituted, the required hair dye is supplied from the occluding part 51 occluding the hair dye of the present invention in the hair dye storing part 50a to a tip part of the feed 52 which is an applying part, and it does not cause "blobbing" and involuntary discharge of liquid. It can be the applicator for hair which is excellent in carrying and handling and excellent as well in usability, water resistance and a cumulative hair dyeing property and in which the comb-like feed 52 and the comb part 53 each can detachably be provided, so that assembling is facilitated.

FIG. 7 to FIG. 8 show an applicator D for hair showing another example of the embodiment of an applicator for hair in which the hair dye of the present invention is used.

The above applicator D for hair comprises, as shown in FIG. 7 and FIG. 8, a pedestal body 60 which is an operating part of the applicator, a receiving member 61 which comprises a plate receiving part 61a and an elastic member 61b comprising a spring member and which is mounted on an upper surface 60a of the above pedestal body 60, a plate receiving member 62, a hair dye storing body 63, an occluding body 64 which occludes the hair dye of the present invention and which is mounted in the above hair dye storing body 63, a comb main body 65 having comb parts 65a, 65a ... on a periphery and a cap member 66, and the hair dye storing body 63 in which the occluding body 64 occluding the hair dye is mounted is installed in the comb main body 65.

In the applicator D for hair thus constituted, the occluding body 64 occluding the hair dye of the present invention is present in the inside of the peripheral comb parts 65a, and therefore the applicator for hair which can dye hair easily and surely while combing the hair with the comb parts 65a ... is obtained. It can be the applicator for hair which is excellent in carrying and handling and excellent as well in usability, water resistance and a cumulative hair dyeing property and in which the comb-like comb main body 65 and the occluding body 64 can detachably be provided, so that assembling is facilitated.

EXAMPLES

Next, the present invention shall be explained in further details with reference to test examples (examples and comparative examples), but the present invention shall not be restricted by the following examples.

Examples 1 to 23 and Comparative Examples 1 to 12

Components were homogeneously mixed and stirred according to recipes shown in the following Table 1 to Table 3 by means of a general purpose propeller mixer to prepare the respective hair dyes.

The respective hair dyes obtained in Examples 1 to 23 and Comparative Examples 1 to 12 described above were measured for a pH and a viscosity by the following methods.

The results thereof are shown in the following Tables 1 to 3.

Measuring Method of pH:

The pH (25° C.) was measured according to a conventional method by means of a glass electrode pH meter.

Evaluation Method of Viscosity:

The respective viscosities at 25° C. were measured by means of an ELD type viscometer or an EMD type viscometer (both manufactured by Toki Sangyo Co., Ltd.). The viscosities exceeding 12 mPa·s were measured by means of the EMD type viscometer.

Then, the respective hair dyes obtained above were used to evaluate water resistance, a cumulative hair dyeing property (5 times), an applying performance, low temperature stability, a drying property and an irritating property by the following methods. Further, the hair dyes were overall evaluated from the evaluations of the above six items based on the following evaluation criteria.

The results thereof are shown in the following Tables 1 to 3.

Constitution of applicator for hair: based on FIG. 2 to 6:
Feeds: fiber bundle, made of polyester
Comb parts: molded article made of polypropylene Evaluation Method of Water Resistance:

After about 0.4 g of the hair dye was applied on 2 g of the hairs and dried at room temperature for 120 minutes (hereinafter referred to merely as [after applied on the hairs and dried]), a filter paper wetted with water was pressed thereon to evaluate the degree of the color transferred onto the filter paper according to the following evaluation criteria.

Evaluation Criteria
⊚: not transferred at all onto filter paper
○: slightly transferred onto filter paper
Δ: a little densely transferred onto filter paper
X: densely transferred onto filter paper Evaluation Method of Cumulative Hair Dyeing Property:

After applied on 1 g of a hair bundle and dried, twice washing of the hairs was repeated five times, and then the cumulative hair dyeing property was evaluated according to the following evaluation criteria.

Evaluation Criteria
⊚: same as commercially available oxidizing hair dyes
○: no problems on practical use
Δ: a little difficult to be dyed
X: not dyed Evaluation Method of Applying Performance:

The applying performance observed when applied on hair by means of the applicator (sliver vessel) for hair was evaluated according to the following evaluation criteria.

Evaluation Criteria
○: a liquid amount adhered onto the hair is reasonable, and the applying performance is good
Δ: a liquid amount adhered onto the hair is somewhat small, and the applying performance is a little inferior
X: a liquid amount adhered onto the hair is small, and the applying performance is inferior Evaluation Method of Low Temperature Stability:

Each 100 ml of the respective hair dyes was put in a transparent vessel equipped with a cap and stored at −10° C. for one month, and then it was observed with the naked eyes and evaluated according to the following evaluation criteria.

Evaluation Criteria
○: no precipitates are observed, and the same state as immediately after produced is maintained
Δ: precipitates are observed a little but stay in a level providing no problems on the quality and the usability
X: settling (precipitates) is observed Evaluation Method of Drying Property after Applying The hair dye 0.2 g was applied on 1 g of a human hair bundle and touched with a finger every 30 seconds to measure time passing until it did not adhere onto the finger, and it was evaluated according to the following evaluation criteria.

Evaluation Criteria
⊚: 2 minutes or shorter
○: 4 minutes or shorter
Δ: 6 minutes or shorter
X: exceeding 6 minutes Evaluation Method of Irritating Property:

Among the hair dyes prepared in Examples 1 to 23 and Comparative Examples 1 to 12, 32 applicable samples excluding the hair dyes prepared in Comparative Examples 3 and 9 were applied on the hair in positions where they are as close as possible to the skins of 20 monitors to confirm whether or not they felt irritation, and it was evaluated according to the following evaluation criteria.

Evaluation Criteria
○: no monitor felt irritation
Δ: 1 to 6 monitors felt irritation
X: 7 or more monitors felt irritation Overall Evaluation Method:

Evaluated from the respective evaluations (6 evaluations) of the water resistance, the cumulative hair dyeing property (5 times), the applying performance, the low temperature stability, the drying property and the irritating property each described above according to the following evaluation criteria.

Evaluation Criteria
⊚: all of 6 evaluations are marked with ○ or better
○: 3 or more of 6 evaluations is marked with ○ or better, and 3 or less is marked with Δ or better
Δ: 2 or less of 6 evaluations is marked with ○ or better, and 4 or less is marked with Δ or better
X: one or more of 6 evaluations is marked with X

TABLE 1

| | Test No. | | | | | | | | | | |
|---|---|---|---|---|---|---|---|---|---|---|---|
| | 1 | 2 | 3 | 4 | 5 | 6 | 7 | 8 | 9 Comparative | 10 Comparative | 11 |
| | Example | | | | | | | | Example | | Example |
| | 1 | 2 | 3 | 4 | 5 | 6 | 7 | 8 | 1 | 2 | 9 |
| Black No. 401 | 0.2 | 0.2 | 0.09 | 0.09 | 0.03 | 0.1665 | 0.1665 | 0.1665 | 0.36 | 0.36 | 0.148 |
| Purple No. 401 | 0.12 | 0.12 | 0.2 | 0.2 | 0.26 | 0.099 | 0.099 | 0.099 | 0.24 | 0.24 | 0.088 |
| Orange No. 205 | 0.2 | 0.2 | 0.26 | 0.26 | 0.26 | 0.1665 | 0.1665 | 0.1665 | 0.37 | 0.37 | 0.148 |
| Red No. 207 | 0.03 | 0.03 | | | | 0.018 | 0.018 | 0.018 | 0.05 | 0.05 | 0.016 |
| Dye total | 0.55 | 0.55 | 0.55 | 0.55 | 0.55 | 0.45 | 0.45 | 0.45 | 1.02 | 1.02 | 0.4 |
| Refined water | 49.85 | 49.85 | 36.85 | 36.85 | 43.15 | 47 | 47 | 47 | 42.57 | 43.48 | 49.85 |
| Ethanol | 27.6 | 27.6 | 40.6 | 40.6 | 31.3 | 32.55 | 36.05 | 32.55 | 35 | 39 | 31.75 |

TABLE 1-continued

| | Test No. | | | | | | | | 9 Comparative Example | 10 Comparative Example | 11 Example |
|---|---|---|---|---|---|---|---|---|---|---|---|
| | 1 | 2 | 3 | 4 | 5 Example | 6 | 7 | 8 | 1 | 2 | 9 |
| | 1 | 2 | 3 | 4 | 5 | 6 | 7 | 8 | 1 | 2 | 9 |
| Benzyl alcohol | 10 | 10 | 10 | 10 | 10 | 10 | 10 | 10 | 10 | 10 | 10 |
| N-methyl-2-pyrrolidone | | | | | | | | | | | |
| Propylene carbonate | | | | | | | | | | | |
| 70% glycolic acid aqueous solution | 5 | 5 | 5 | 5 | 5 | 5 | 1.5 | 5 | 5 | 5 | 5 |
| Citric acid | | | | | | | | | | | |
| Lactic acid | | | | | | | | | | | |
| STYLEZE W-10 (resin solid content: 10%) | 7 | 7 | 7 | 7 | 10 | 5 | 5 | 5 | 6.41 | 1.5 | 3 |
| MERQUAT 280 (NALCO) (resin solid content: 40%) | | | | | | | | | | | |
| CELQUAT SC240C (powder) | | | | | | | | | | | |
| Total | 100 | 100 | 100 | 100 | 100 | 100 | 100 | 100 | 100 | 100 | 100 |
| Satisfaction of $0.1(x+1) \leq y \leq 0.264x + 0.4$ | ○ | ○ | ○ | ○ | ○ | ○ | ○ | ○ | — | — | ○ |
| Water total amount (%) | 57.65 | 57.65 | 44.65 | 44.65 | 53.65 | 53 | 51.5 | 51.5 | 44.07 | 44.98 | 54.05 |
| Ethanol total amount (%) | 27.6 | 27.6 | 40.6 | 40.6 | 31.3 | 32.55 | 36.05 | 32.55 | 35 | 39 | 31.75 |
| Water/(water + ethanol) | 0.68 | 0.66 | 0.52 | 0.51 | 0.63 | 0.62 | 0.59 | 0.61 | 0.56 | 0.54 | 0.63 |
| Evaluation | | | | | | | | | | | |
| Water resistance | ○ | ○ | ○ | ○ | ○ | ○ | ○ | ○ | X | Δ | ○ |
| Cumulation 5 times | ⊚ | ⊚ | ○ | ○ | ○ | ○ | ○ | ○ | Δ | X | Δ |
| Applying performance | ○ | ○ | ○ | ○ | ○ | ○ | ○ | ○ | ○ | X | ○ |
| Low temperature stability | ○ | ○ | ○ | ○ | ○ | ○ | ○ | ○ | ○ | ○ | ○ |
| Drying property | ○ | ○ | ○ | ○ | ○ | ○ | ○ | ○ | ○ | ○ | ○ |
| Irritating property | ○ | ○ | ○ | ○ | ○ | ○ | ○ | ○ | ○ | ○ | ○ |
| 50 rpm viscosity (mPa·s) | 6 | 6 | 7.6 | 7.6 | 13.5 | 4.46 | 4.46 | 4.46 | 6.41 | 120 | 4.34 |
| pH | 2.69 | 2.68 | 2.78 | 2.75 | 2.72 | 2.7 | 2.83 | 2.74 | 3.02 | 3.11 | 2.68 |
| Overall evaluation | ⊚ | ⊚ | ⊚ | ⊚ | ⊚ | ⊚ | ⊚ | ⊚ | X | X | ○ |

TABLE 2

| | Test No. | | | | | | | | | | |
|---|---|---|---|---|---|---|---|---|---|---|---|
| | 12 Example | 13 Comparative Example | 14 Example | 15 Comparative Example | 16 Example | 17 Comparative Example | 18 Comparative Example | 19 Example | 20 Example | 21 Comparative Example | 22 Example |
| | 10 | 3 | 11 | 4 | 12 | 5 | 6 | 13 | 14 | 7 | 15 |
| Black No. 401 | 0.37 | 0.2 | 0.2 | 1.27 | 1.09 | 0.018 | 0.2 | 0.2 | 0.2 | 0.2 | 0.2 |
| Purple No. 401 | 0.22 | 0.12 | 0.12 | 0.76 | 0.65 | 0.011 | 0.12 | 0.12 | 0.12 | 0.12 | 0.12 |
| Orange No. 205 | 0.37 | 0.2 | 0.2 | 1.27 | 1.09 | 0.018 | 0.2 | 0.2 | 0.2 | 0.2 | 0.2 |
| Red No. 207 | 0.04 | 0.03 | 0.03 | 0.19 | 0.16 | 0.003 | 0.03 | 0.03 | 0.03 | 0.03 | 0.03 |
| Dye total | 1 | 0.55 | 0.55 | 3.50 | 3.00 | 0.050 | 0.55 | 0.55 | 0.55 | 0.55 | 0.55 |
| Refined water | 42.35 | 59.85 | 29.85 | 25.8 | 26.1 | 45.1 | 50.55 | 49.05 | 47.85 | 35.85 | 40.65 |
| Ethanol | 31.65 | 17.6 | 47.6 | 30.7 | 30.9 | 32.85 | 36.4 | 35.4 | 34.6 | 26.6 | 28.8 |

TABLE 2-continued

| | Test No. | | | | | | | | | | |
|---|---|---|---|---|---|---|---|---|---|---|---|
| | 12 Example | 13 Comparative Example | 14 Example | 15 Comparative Example | 16 Example | 17 Comparative Example | 18 Comparative Example | 19 Example | 20 Example | 21 Comparative Example | 22 Example |
| | 10 | 3 | 11 | 4 | 12 | 5 | 6 | 13 | 14 | 7 | 15 |
| Benzyl alcohol | 10 | 10 | 10 | 10 | 10 | 10 | 0.5 | 3 | 5 | 25 | 18 |
| N-methyl-2-pyrrolidone | | | | | | | | | | | |
| Propylene carbonate | | | | | | | | | | | |
| 70% glycolic acid aqueous solution | 5 | 5 | 5 | 5 | 5 | 5 | 5 | 5 | 5 | 5 | 5 |
| Citric acid | | | | | | | | | | | |
| Lactic acid | | | | | | | | | | | |
| STYLEZE W-10 (resin solid content: 10%) | 10 | 7 | 7 | 25 | 25 | 7 | 7 | 7 | 7 | 7 | 7 |
| MERQUAT 280 (NALCO) (resin solid content: 40%) | | | | | | | | | | | |
| CELQUAT SC240C (powder) | | | | | | | | | | | |
| Total | 100 | 100 | 100 | 100 | 100 | 100 | 100 | 100 | 100 | 100 | 100 |
| Satisfaction of $0.1(x+1) \leq y \leq 0.264x + 0.4$ | X | ◯ | ◯ | X | X | X | ◯ | ◯ | ◯ | ◯ | ◯ |
| Water total amount (%) | 52.85 | 67.65 | 37.65 | 49.8 | 50.1 | 52.9 | 58.35 | 56.85 | 55.65 | 43.65 | 48.45 |
| Ethanol total amount (%) | 31.65 | 17.6 | 47.6 | 30.7 | 30.9 | 32.85 | 36.4 | 35.4 | 34.6 | 26.6 | 28.8 |
| Water/(water + ethanol) | 0.63 | 0.79 | 0.44 | 0.62 | 0.62 | 0.62 | 0.62 | 0.62 | 0.62 | 0.62 | 0.63 |
| Evaluation | | | | | | | | | | | |
| Water resistance | Δ | — | ◯ | X | Δ | ◯ | ◯ | ◯ | ◯ | ◯ | ◯ |
| Cumulation 5 times | ◯ | — | Δ | Δ | Δ | X | X | Δ | ◯ | ◯ | ◯ |
| Applying performance | ◯ | — | ◯ | Δ | Δ | ◯ | ◯ | ◯ | ◯ | ◯ | ◯ |
| Low temperature stability | ◯ | — | ◯ | ◯ | ◯ | ◯ | ◯ | ◯ | ◯ | ◯ | ◯ |
| Drying property | ◯ | — | ◯ | ◯ | ◯ | ◯ | ◯ | ◯ | ◯ | X | Δ |
| Irritating property | ◯ | — | ◯ | ◯ | ◯ | ◯ | ◯ | ◯ | ◯ | ◯ | ◯ |
| 50 rpm viscosity (mPa·s) | 4.19 | Settled | 6.11 | 40.32 | 38.76 | 13.52 | 6.2 | 4.77 | 5.13 | 8.62 | 7.51 |
| pH | 2.71 | Settled | 2.88 | 2.92 | 2.92 | 2.75 | 2.61 | 2.63 | 2.71 | 2.74 | 2.7 |
| Overall evaluation | ◯ | X | ◯ | X | ◯ | X | X | ◯ | ◎ | X | ◯ |

TABLE 3

| | Test No. | | | | | | | | | | | | |
|---|---|---|---|---|---|---|---|---|---|---|---|---|---|
| | 23 Example | 24 Comparative Example | 25 Example | 26 Comparative Example | 27 Example | 28 Comparative Example | 29 Comparative Example | 30 Example | 31 Example | 32 Comparative Example | 33 Example | 34 Example | 35 Example |
| | 16 | 8 | 17 | 9 | 18 | 10 | 11 | 19 | 20 | 12 | 21 | 22 | 23 |
| Black No. 401 | 0.2 | 0.18 | 0.18 | 0.2 | 0.2 | 0.18 | 0.2 | 0.2 | 0.2 | 0.2 | 0.056 | 0.2 | 0.18 |
| Purple No. 401 | 0.12 | 0.11 | 0.11 | 0.12 | 0.12 | 0.11 | 0.12 | 0.12 | 0.12 | 0.12 | 0.033 | 0.12 | 0.11 |
| Orange No. 205 | 0.2 | 0.18 | 0.18 | 0.2 | 0.2 | 0.18 | 0.2 | 0.2 | 0.2 | 0.2 | 0.055 | 0.2 | 0.18 |
| Red No. 207 | 0.03 | 0.03 | 0.03 | 0.03 | 0.03 | 0.03 | 0.03 | 0.03 | 0.03 | 0.03 | 0.006 | 0.03 | 0.03 |
| Dye total | 0.55 | 0.5 | 0.5 | 0.55 | 0.55 | 0.5 | 0.55 | 0.55 | 0.55 | 0.55 | 0.15 | 0.55 | 0.5 |
| Refined water | 41.85 | 17.5 | 25.3 | 65.25 | 49.95 | 12 | 49.85 | 49.85 | 44.85 | 43.35 | 44.85 | 52.05 | 16.4 |
| Ethanol | 31.6 | 65 | 52.2 | 12.2 | 27.5 | 57.5 | 32.55 | 32.1 | 22.6 | 26.6 | 33 | 23.3 | 59.1 |
| Benzyl alcohol | 14 | 5 | 10 | 10 | 10 | 18 | 10 | 10 | 10 | 10 | 10 | 12.1 | 12 |
| N-methyl-2-pyrrolidone | | | | | | | | | | | | | |

TABLE 3-continued

| | Test No. | | | | | | | | | | | | |
|---|---|---|---|---|---|---|---|---|---|---|---|---|---|
| | 23 Example 16 | 24 Comparative Example 8 | 25 Example 17 | 26 Comparative Example 9 | 27 Example 18 | 28 Comparative Example 10 | 29 Comparative Example 11 | 30 Example 19 | 31 Example 20 | 32 Comparative Example 12 | 33 Example 21 | 34 Example 22 | 35 Example 23 |
| Propylene carbonate | | | | | | | | | | | | | |
| 70% glycolic acid aqueous solution | 5 | 5 | 5 | 5 | 5 | 5 | 0.05 | 0.5 | 15 | 12.5 | 5 | 5 | 5 |
| Citric acid | | | | | | | | | | | | | |
| Lactic acid | | | | | | | | | | | | | |
| STYLEZE W-10 (resin solid content: 10%) | 7 | 7 | 7 | 7 | 7 | 7 | 7 | 7 | 7 | 7 | 7 | 7 | 7 |
| MERQUAT 280 (NALCO) (resin solid content: 40%) | | | | | | | | | | | | | |
| CELQUAT SC240C (powder) | | | | | | | | | | | | | |
| Total | 100 | 100 | 100 | 100 | 100 | 100 | 100 | 100 | 100 | 100 | 100 | 100 | 100 |
| Satisfaction of 0.1 (x + 1) ≦ y ≦ 0.264x + 0.4 | ◯ | ◯ | ◯ | ◯ | ◯ | ◯ | ◯ | ◯ | ◯ | ◯ | X | ◯ | ◯ |
| Water total amount (%) | 49.65 | 25.3 | 33.1 | 73.05 | 57.75 | 19.8 | 56.165 | 56.3 | 55.65 | 49.65 | 52.65 | 59.85 | 24.2 |
| Ethanol total amount (%) | 31.6 | 65 | 52.2 | 12.2 | 27.5 | 57.5 | 32.55 | 32.1 | 22.6 | 26.6 | 33 | 23.3 | 59.1 |
| Water/(water + ethanol) | 0.61 | 0.28 | 0.39 | 0.86 | 0.68 | 0.26 | 0.63 | 0.64 | 0.71 | 0.65 | 0.61 | 0.72 | 0.29 |
| Evaluation | | | | | | | | | | | | | |
| Water resistance | ◯ | ◯ | ◯ | — | ◯ | ◯ | ◯ | ◯ | ◯ | ◯ | ◎ | ◯ | ◯ |
| Cumulation 5 times | ◯ | X | Δ | — | ◯ | X | X | Δ | ◎ | ◎ | Δ | ◎ | Δ |
| Applying performance | ◯ | ◯ | ◯ | — | ◯ | ◯ | ◯ | ◯ | ◯ | ◯ | ◯ | ◯ | ◯ |
| Low temperature stability | ◯ | ◯ | ◯ | — | ◯ | Δ | ◯ | ◯ | ◯ | ◯ | ◯ | Δ | ◯ |
| Drying property | ◯ | ◎ | ◎ | — | Δ | Δ | ◯ | ◯ | ◯ | ◯ | ◯ | Δ | ◯ |
| Irritating property | ◯ | ◯ | ◯ | — | ◯ | ◯ | ◯ | ◯ | Δ | X | ◯ | ◯ | ◯ |
| 50 rpm viscosity (mPa·s) | 6.75 | 6.16 | 7.36 | Settled | 6.05 | 6.59 | 6.31 | 6.22 | 5.94 | 5.88 | 11.24 | 4.21 | 7.75 |
| pH | 2.68 | 3.31 | 3.11 | Settled | 2.6 | 3.4 | 4.15 | 3.46 | 2.29 | 1.91 | 2.64 | 2.22 | 3.02 |
| Overall evaluation | ◎ | X | ◯ | X | ◯ | X | X | ◯ | ◯ | X | ◯ | Δ | ◯ |

As apparent from the results shown in Tables 1 to 3 described above, it has found that the hair dyes prepared in Examples 1 to 23 each falling in the scope of the present invention are excellent, as compared with the hair dyes prepared in Comparative Examples 1 to 12 each falling outside the scope of the present invention, in water resistance, a cumulative hair dyeing property (5 times), an applying performance, low temperature stability and a drying property and that they are free from skin irritation.

To observe individually the comparative examples, resins other than the resin comprising the terpolymer are used in Comparative Examples 1 and 2. That is, MERQUAT 280 (NALCO Company; Polyquaternium-22, resin solid content: 40%, acrylic acid: 20%, diallyldimethylamonium chloride: 80%) was used in Comparative Example 1, and in this case, the hair dye is inferior in water resistance and somewhat inferior as well in a cumulative hair dyeing property. Comparative Example 2 is a case in which CELQUAT SC240C (National Starch & Chemical Company; Polyquaternium-10, powder, Polyquaternium-10, cationic hydroxycellulose) was used, and in this case, it can be found that the hair dye is a little inferior as well in water resistance and inferior in a cumulative hair dyeing property and an applying performance.

Further, it can be found that settling is caused in Comparative Examples 3 and 9 in which a content of water is large and that the effects of the present invention (water resistance, cumulative hair dyeing property (5 times), applying performance, low temperature stability and drying property) can not be exerted in Comparative Example 4 in which a content of the dye is large, Comparative Example 5 in which a content of the dye is small, Comparative Examples 6 and 7 in which a content of the hair dyeing auxiliary agent is small or large, Comparative Examples 8 and 9 in which a content of the lower alcohol is large or small, Comparative Example 10 in which a content of water is small and Comparative Examples 11 and 12 in which a pH of the hair dye is deviated from a range of 2 to 4.

EXPLANATION OF LETTERS OR NUMERALS

Figure 1:
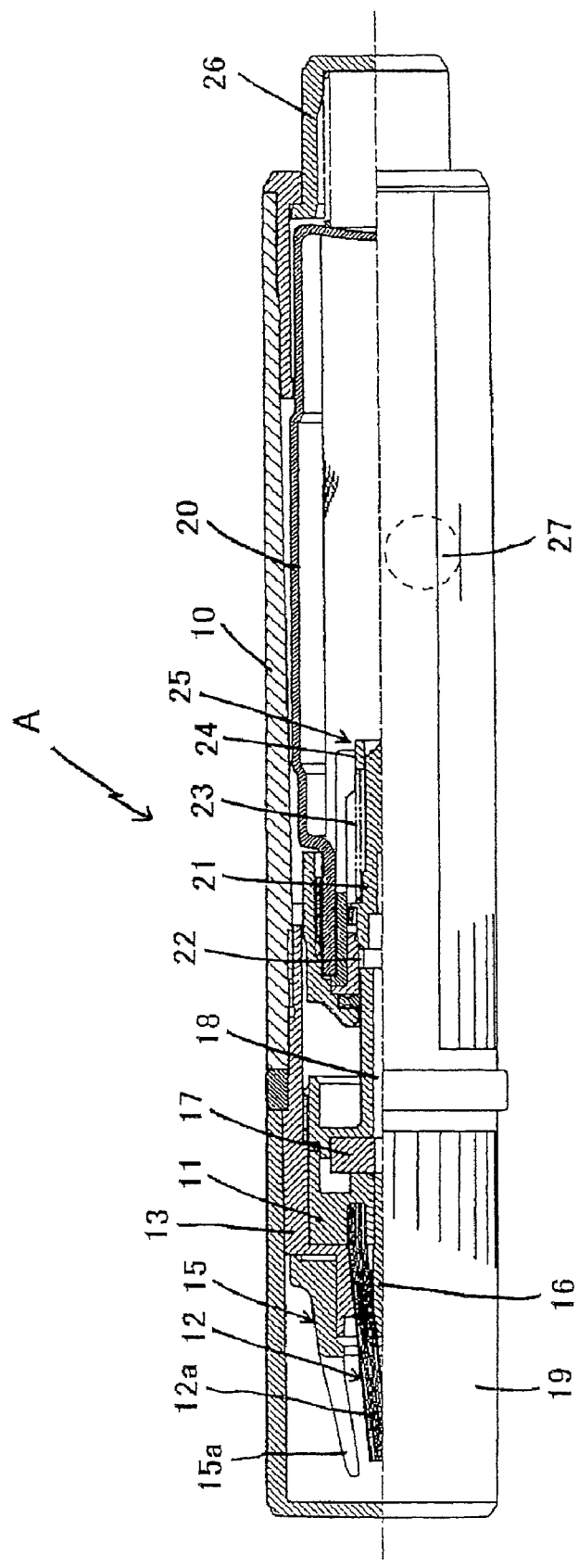
FIG. 1 is a partial vertical cross-sectional drawing of the applicator for hair showing one example of the embodiments of the present invention.
Figure 2:
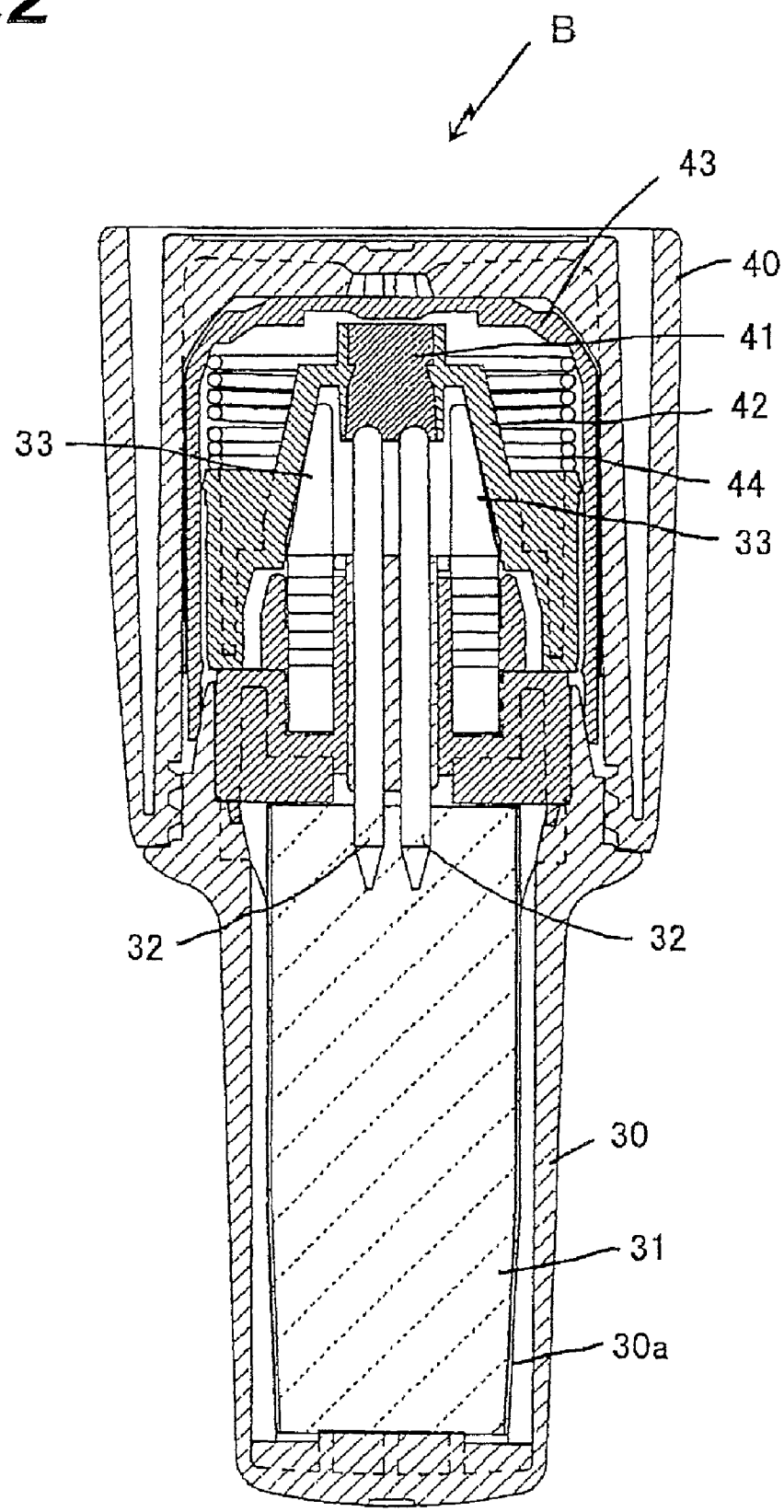
FIG. 2 is a vertical cross-sectional drawing in a side view aspect of an applicator for hair showing another example of the embodiments of the present invention.
Figure 3:
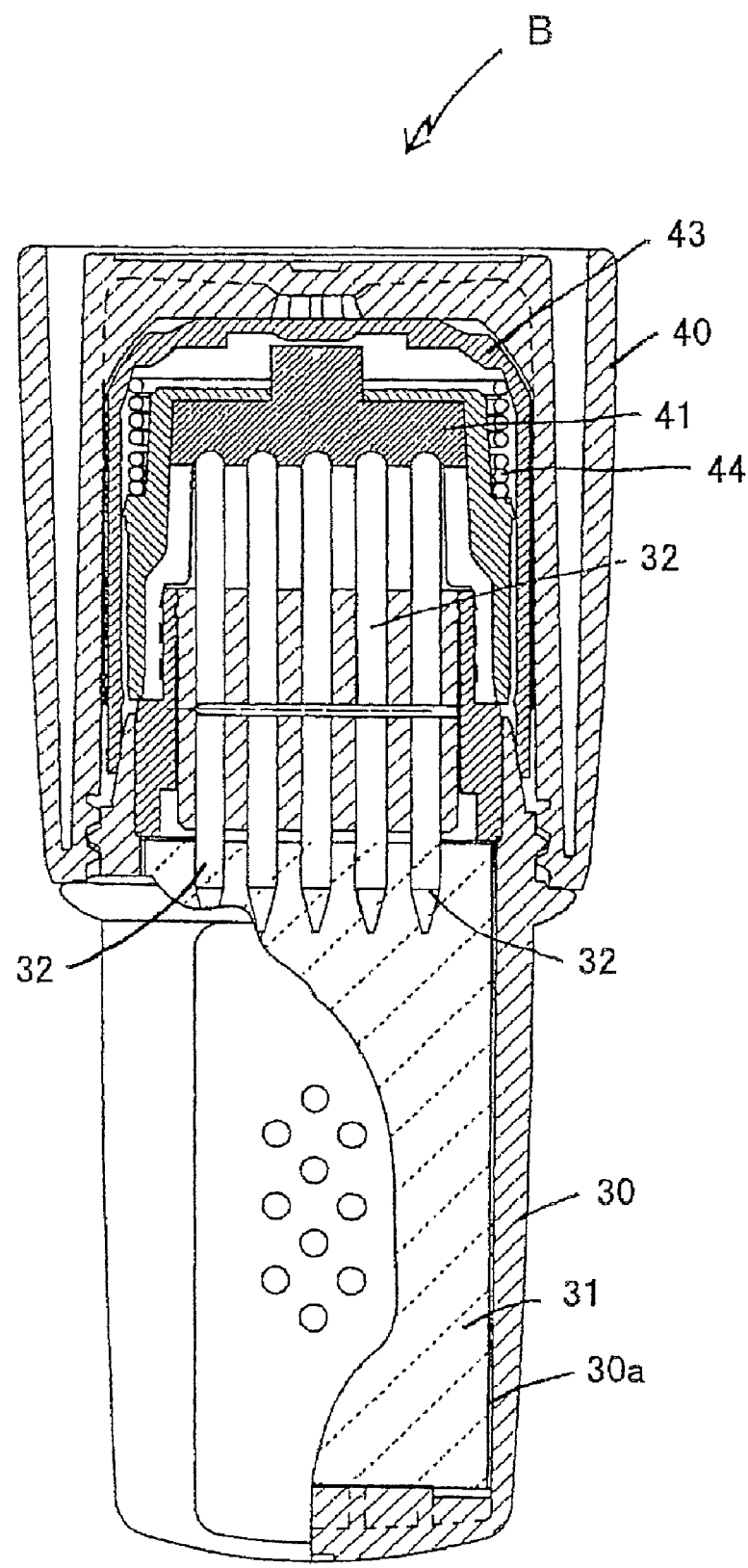
FIG. 3 is a vertical cross-sectional drawing in a front view aspect of the applicator for hair shown in FIG. 2.
Figure 4:
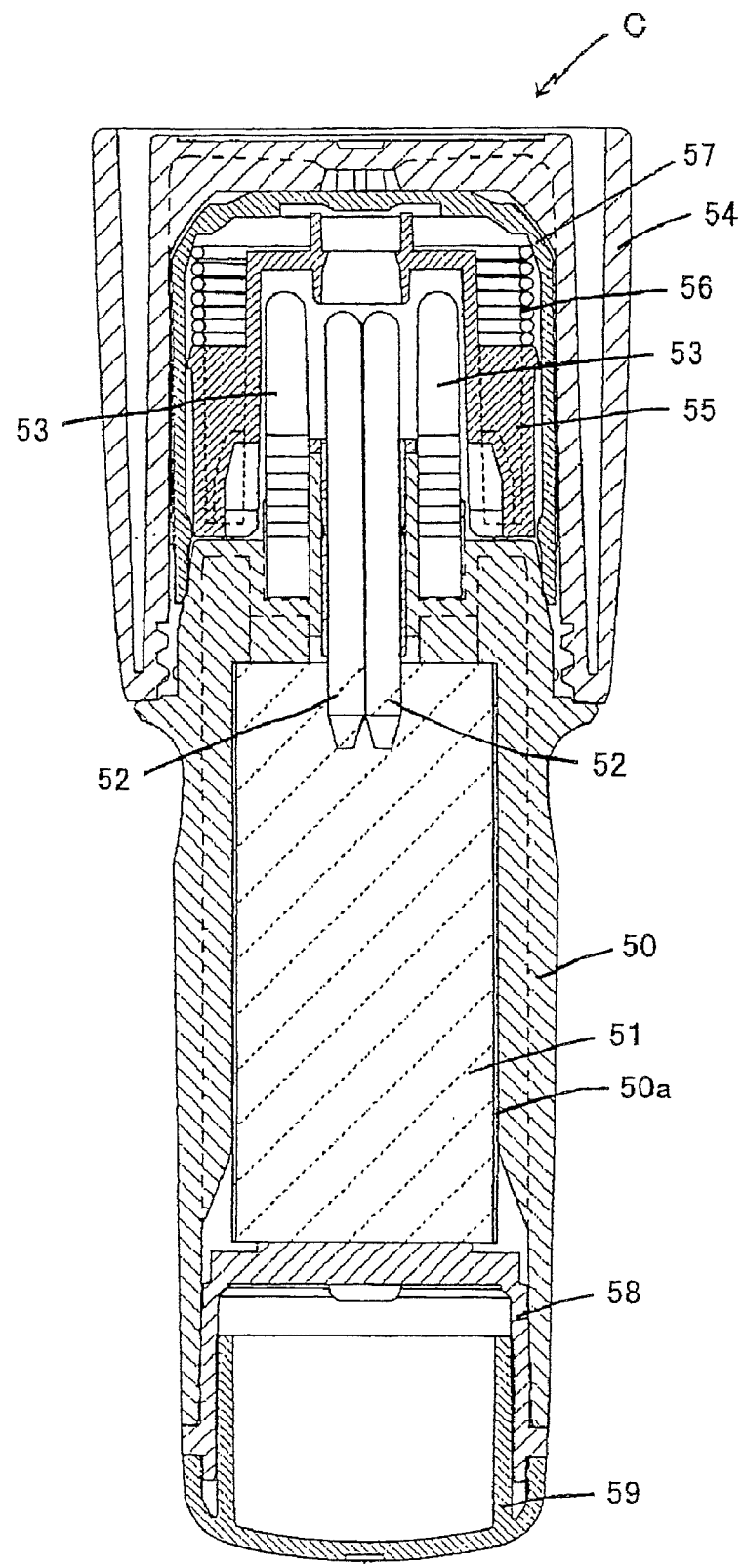
FIG. 4 is a vertical cross-sectional drawing in a side view aspect of an applicator for hair showing another example of the embodiments of the present invention.
Figure 5A:
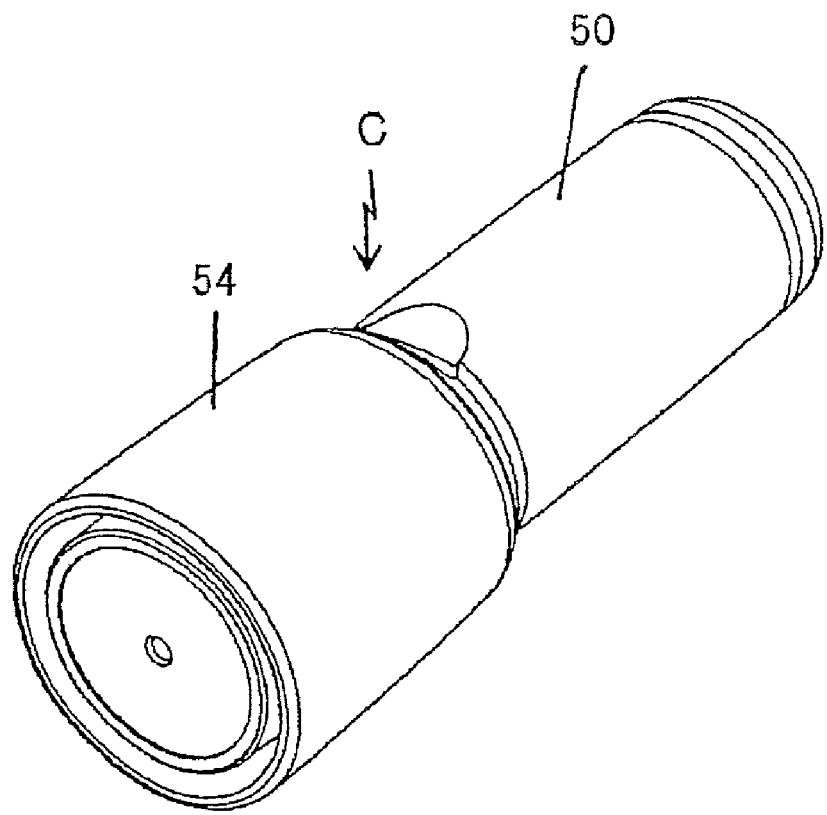
FIG. 5A is a perspective drawing of the applicator for hair shown in FIG. 4.
Figure 5B:
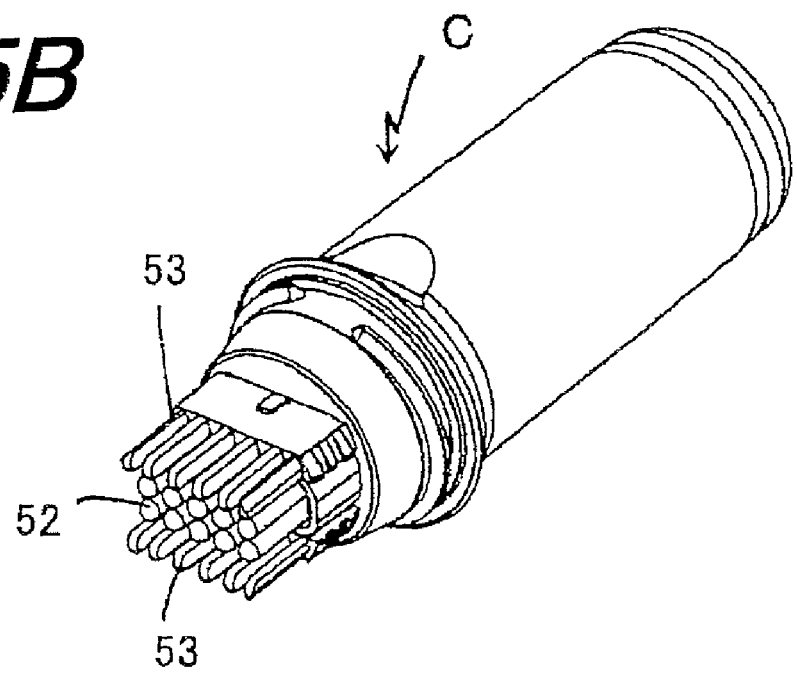
FIG. 5B is a perspective drawing showing a state in which a cap body is removed.
Figure 6:
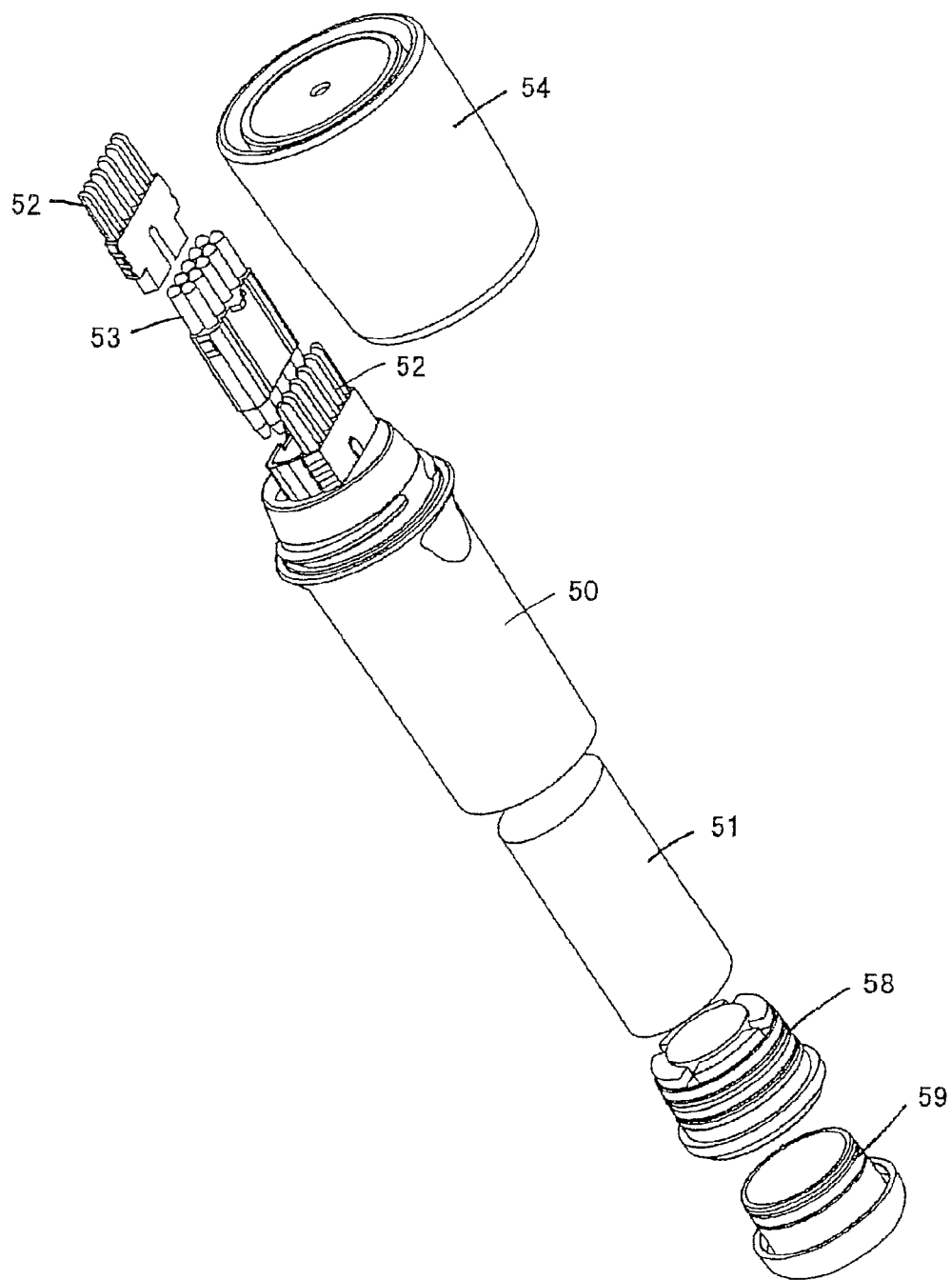
FIG. 6 is an exploded perspective drawing of the applicator for hair shown in FIG. 4.
Figure 7:
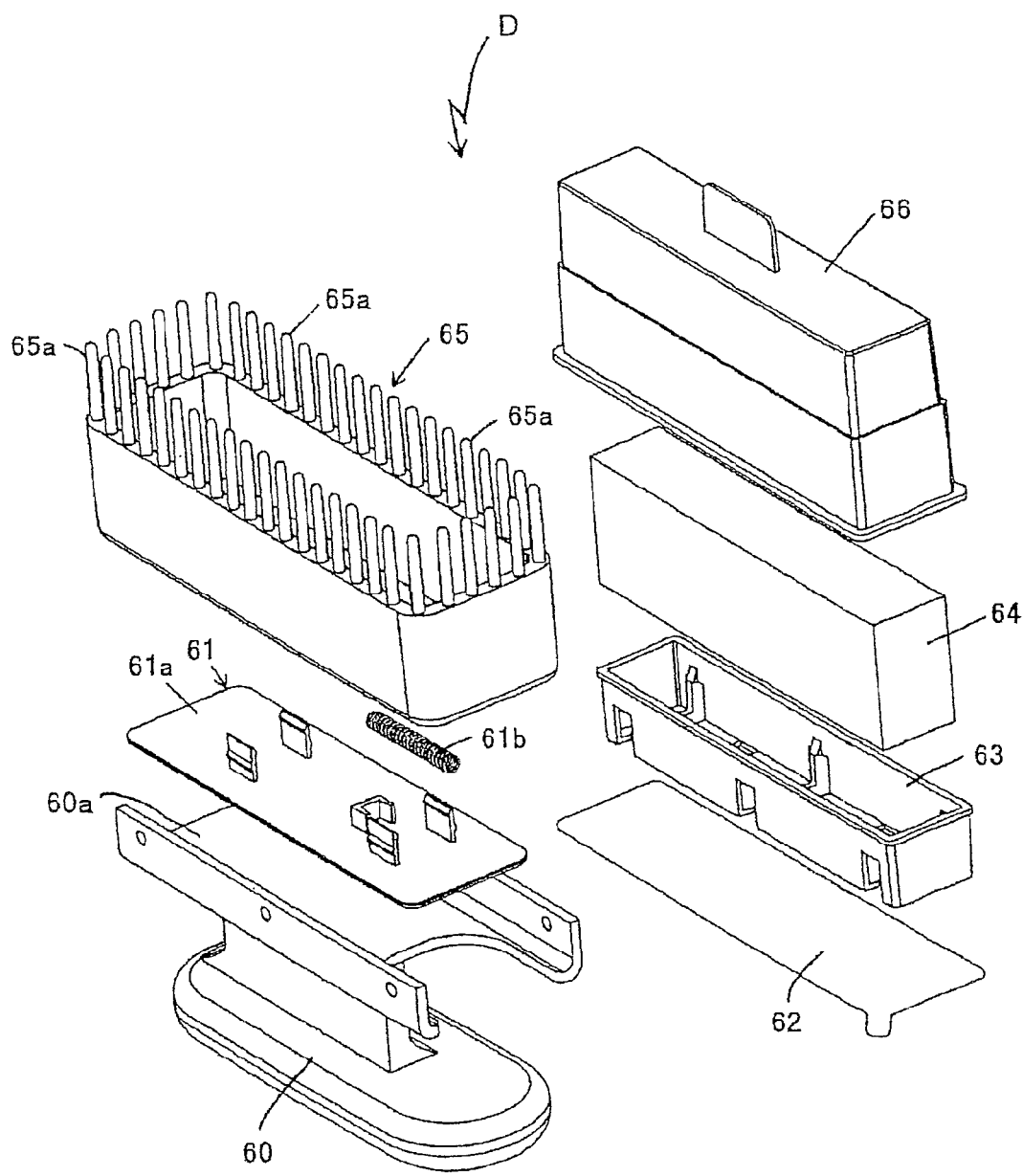
FIG. 7 is a vertical cross-sectional drawing in a side view aspect of an applicator for hair showing another example of the embodiments of the present invention.
Figure 8A:
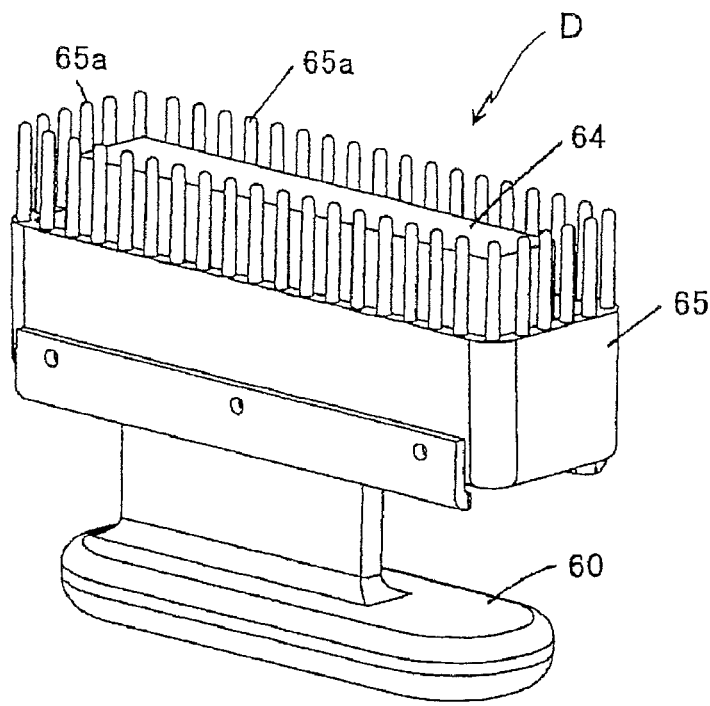
FIG. 8A is a perspective drawing of the assembled applicator for hair shown in FIG. 7.
Figure 8B:
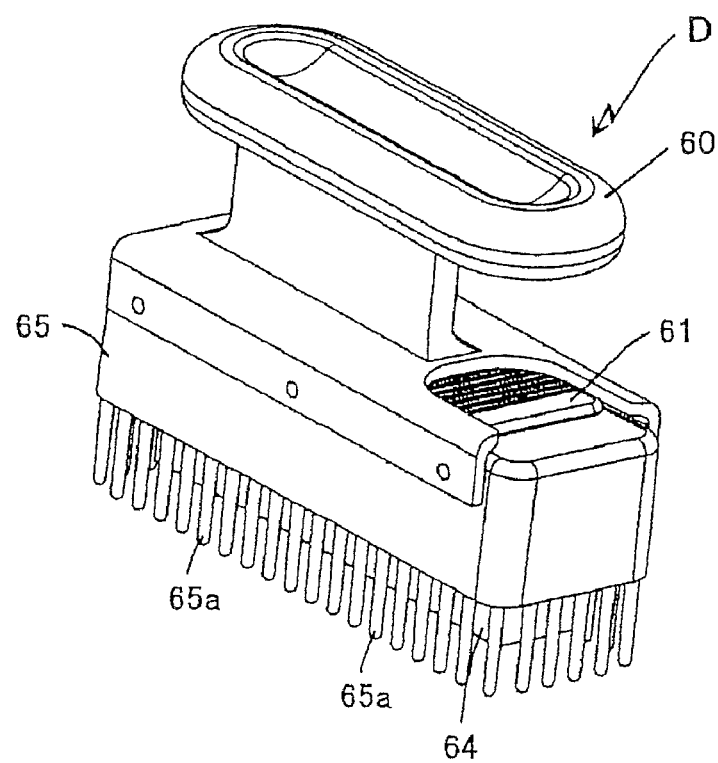
FIG. 8B is a perspective drawing of the applicator for hair observed from a bottom part thereof.

A: Applicator for hair
10: Applicator main body
12: Feed
13: Comb part

What is claimed is:

1. A hair dye comprising 0.1 to 3.0% by weight of at least one of aqueous acid dyes and a resin comprising a terpolymer constituted from a vinyl cyclic amide represented by following Formula (I), an acrylic acid derivative represented by following Formula (II) and a quaternary derivative of acrylic acid represented by following Formula (III), wherein a content of the resin is 0.1 to 2.5% by weight in terms of a solid content; and the hair dye further comprises 1.0 to 20% by weight of a hair dyeing auxiliary agent, 20 to 60% by weight of a lower alcohol and 20 to 60% by weight of water and has a pH of 2 to 4:

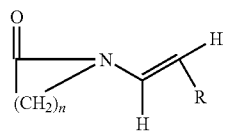

(in Formula (I), n is an integer of 3 to 6, and R represents a hydrogen atom or an alkyl group having 1 to 5 carbon atoms);

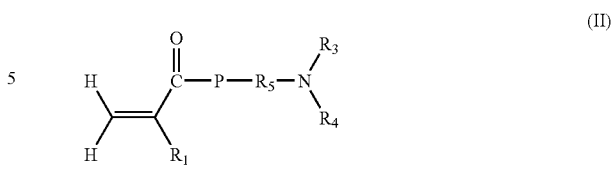

(in Formula (II), P is an oxygen atom or $NR_2$; $R_1$, $R_2$, $R_3$ and $R_4$ each are a hydrogen atom or an alkyl group having 1 to 5 carbon atoms, and they may be the same or different; and $R_5$ represents an alkylalkylene group having 2 to 16 carbon atoms);

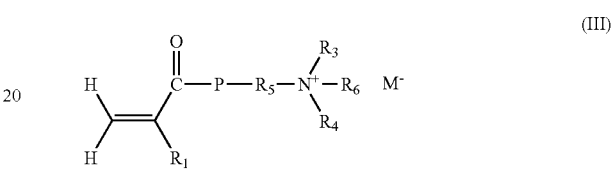

(in Formula (III), P is an oxygen atom or $NR_2$; $R_1$, $R_2$, $R_3$ and $R_4$ each are a hydrogen atom or an alkyl group having 1 to 5 carbon atoms, and they may be the same or different; $R_5$ represents an alkylalkylene group having 2 to 16 carbon atoms; $R_6$ is an alkyl group having 9 to 24 carbon atoms; and M represents a halide, tosylate or phosphoric acid anion).

2. The hair dye as described in claim 1, wherein the resin is constituted from 60 to 90% by weight of a vinyl cyclic amide represented by Formula (I), 5 to 30% by weight of an acrylic acid derivative represented by Formula (II) and 1 to 30% by weight of a quaternary derivative of acrylic acid represented by Formula (III).

3. The hair dye as described in claim 1, wherein the resin has a weight average molecular weight of 400,000 to 800,000.

4. The hair dye as described in claim 1, wherein a content ratio y (% by weight) of the aqueous acid dye satisfies the following Formula (IV) assuming that a solid content of the resin is x (% by weight):

$$0.1(x+1) < y \leq 0.264x + 0.4 \qquad (IV).$$

5. The hair dye as described in claim 1, wherein a content ratio (A)/[(A)+(B)] of water (A) to the lower alcohol (B) is 0.3 to 0.8 in terms of a weight ratio.

6. The hair dye as described in claim 1, wherein the hair dyeing auxiliary agent is at least one selected from monohydric alcohols, polyhydric alcohols, ether alcohols, lower alkylene carbonates, N-alkylpyrrolidones and lactones.

7. The hair dye as described in claim 1, wherein a viscosity of the hair dye is 2 to 50 mPa·s.

8. An applicator for hair having a storing part for storing the hair dye as described in claim 1.

9. The applicator for hair as described in claim 8, wherein an applying main body part comprising an applying body for applying a hair dye on hair and a comb part disposed on a periphery of the applying body is mounted at a tip part of an applicator main body.

* * * * *

UNITED STATES PATENT AND TRADEMARK OFFICE
CERTIFICATE OF CORRECTION

| | | |
|---|---|---|
| PATENT NO. | : 7,803,198 B2 | Page 1 of 1 |
| APPLICATION NO. | : 12/526862 | |
| DATED | : September 28, 2010 | |
| INVENTOR(S) | : Takashi Umeno, Keiichiro Takachiyo and Hiroaki Koyama | |

It is certified that error appears in the above-identified patent and that said Letters Patent is hereby corrected as shown below:

On the Title Page of the patent, under item (57) Abstract, please make the following changes:

On the second line of the Abstract, please delete "of";

On the second line of the Abstract, please change "dyes" to --dye--

Signed and Sealed this
Twenty-fifth Day of January, 2011

David J. Kappos
*Director of the United States Patent and Trademark Office*